United States Patent [19]

Antoku et al.

[11] Patent Number: 4,948,799
[45] Date of Patent: Aug. 14, 1990

[54] IMIDE DERIVATIVES, AND THEIR USE IN PHARMACEUTICALS

[75] Inventors: Fujio Antoku, Hyogo; Mayumi Yoshigi; Ikutaro Saji, both of Osaka; Atsuyuki Kojima, Hyogo; Kukuo Ishizumi, Osaka, all of Japan

[73] Assignee: Sumitomo Pharmaceuticals Company, Limited, Osaka, Japan

[21] Appl. No.: 293,440

[22] Filed: Jan. 4, 1989

Related U.S. Application Data

[62] Division of Ser. No. 100,824, Sep. 25, 1987, Pat. No. 4,812,461.

[30] Foreign Application Priority Data

Sep. 26, 1986 [JP] Japan .................................. 61-228795

[51] Int. Cl.$^5$ .................... A61K 31/45; C07D 401/06; C07D 417/14
[52] U.S. Cl. .................................. 514/278; 514/316; 546/16; 546/187; 546/188
[58] Field of Search .......................... 546/16, 187, 188; 540/524; 514/212, 278, 316

[56] References Cited

U.S. PATENT DOCUMENTS 3,106,552  10/1963  Grogan et al. ........................ 546/16
3,171,839   5/1965  Rorig .................................. 546/188

Primary Examiner—Richard A. Schwartz
Assistant Examiner—Bernard I. Dentz
Attorney, Agent, or Firm—Birch, Stewart, Kolasch & Birch

[57] ABSTRACT

An imide derivative of the formula:

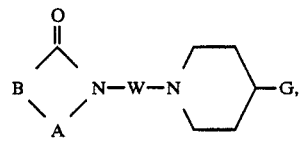

or a pharmaceutically acceptable salt, which is useful as an antipsychotic drug.

8 Claims, No Drawings

IMIDE DERIVATIVES, AND THEIR USE IN PHARMACEUTICALS

This application is a divisional of copending application Ser. No. 100,824, filed on Sept. 25, 1987, now U.S. Pat. No. 4,812,461.

The present invention relates to imide derivatives, and their production and use. More particularly, the invention relates to novel imide derivatives and their salts, their production processes and their use as neuroleptic agents.

The imide derivatives of this invention are represented by the formula:

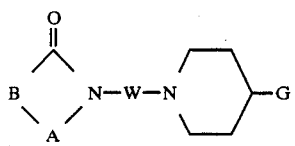

wherein

A is a carbonyl group or a sulfonyl group;
B is either one of the formulas:

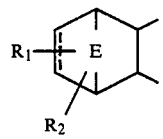

(in which $R_1$ and $R_2$ are each a hydrogen atom, or either one of them is a hydrogen atom and the other is a hydroxyl group, a lower alkyl group or a lower alkanoyloxy group, or $R_1$ and $R_2$ are combined together to represent an oxo group, E is a methylene group, an ethylene group or an oxygen atom and a full line accompanying a broken line (-----) indicates a single bond or a double bond),

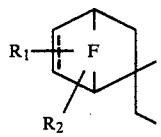

(in which F is a methylene group or an ethylene group and $R_1$, $R_2$ and a full line accompanying a broken line (-----) are each as defined above),

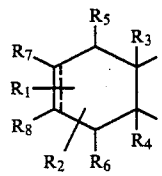

(in which $R_3$, $R_4$, $R_5$, $R_6$, $R_7$ and $R_8$ are each a hydrogen atom or a lower alkyl group and $R_1$, $R_2$ and a full line accompanying a broken line (-----) are each as defined above),

(in which $R_9$ and $R_{10}$ are each a lower alkyl group), or

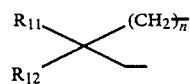

(in which $R_{11}$ and $R_{12}$ are each a lower alkyl group, or they are combined together to form a lower alkylene group and n is an integer of 0, 1 or 2) when A represents a carbonyl group, or a 1,2-phenylene group when A represents a sulfonyl group;

W is a lower alkylene group, a lower alkenylene group, a lower alkynylene group or a lower alkylene group substituted with hydroxyl; and G is a substituted or unsubstituted benzoisothiazolyl group or a group of the formula:

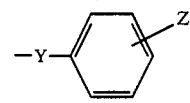

(in which Y is an oxygen atom, a carbonyl group, a methylene group, a group of the formula:

(in which m is an integer of 0, 1 or 2), a group of the formula:

(in which $R_{13}$ is a hydrogen atom, a lower alkyl group or a lower alkanoyl group) or a group of the formula:

and Z is a hydrogen atom, a halogen atom, a lower alkyl group or a lower alkoxy group).

Their salts include acid addition salts, i.e. salts with organic or inorganic acids such as hydrochloric acid, hydrobromic acid, hydroiodic acid, sulfuric acid, acetic adid, oxalic acid, citric acid, malic acid, tartaric acid, fumaric acid and maleic acid.

In the above definitions, the term "lower" is intended to mean a group having usually not more than 8 carbon atoms, preferably not more than 5 carbon atoms. Thus, the lower alkyl group may be straight or branched and covers methyl, ethyl, propyl, isopropyl, butyl, etc. Examples of the lower alkoxy group are methoxy, ethoxy, propoxy, isopropoxy, butoxy, etc. As the lower alkanoyl group, there may be exemplified acetyl, propionyl, butyryl, etc. Examples of the lower alkanoyloxy group are acetoxy, propionyloxy, butyryloxy, etc. The lower alkylene group may be, for instance, methylene, ethylene, trimethylene, propylene, tetramethylene, 2-methyltrimethylene, 2-methyltetramethylene, etc. When the symbol G represents a substituted benzoisothiazolyl group, the substituent may be chosen from lower alkyl, lower alkoxy, halogen (e.g. chlorine, bromine, iodine, fluorine), halogenated lower alkyl (e.g. trifluoromethyl), etc.

As antipsychotic agents, particularly neuroleptics, there have heretofore been used tricyclic compounds such as chlorpromazine (2-chloro-10-(3-dimethylaminopropyl)phenothiazine), butyrophenone compounds such as haloperidol (4-[4-(4-chlorophenyl)-4-hydroxy-1-piperidinyl]-1-(4-fluorophenyl)-1-butanone), etc. However, these conventional neuroleptics produce serious side effects such as catalepsy and hypotension, which cause great problems on their clinical use.

In recent years, some spiroimide compounds have been developed as neuroleptics partly overcoming the drawbacks as seen in conventional neuroleptics. Their typical examples are buspirone (8-[4-(2-pyrimidinyl)-1-piperazinylbutyl]-8-azaspiro[4,5]decane-7,9-dione) and tiaspirone (8-[4-(3-benzisothiazolyl)-1-piperazinylbutyl]-8-azaspiro[4,5]decane-7,9-dione). These spiroimide compounds are alleviated in extrapyramidal side effects such as catalepsy inducing activity in comparison with butyrophenone compounds such as haloperidol. In addition, their anti-dopamine activity, as an indication of neuroleptic activity, are considerably high. For instance, tiaspirone shows anti-dopamine activity stronger than chlorpromazine and nearly equal to haloperidol on intraperitoneal administration in an anti-climbing behavior test using apomorphine. Unexpectedly, however, it was found that the anti-dopamine activity of tiaspirone is drastically reduced on oral administration.

As the result of an extensive study, it has now been found that the imide derivatives (I) of the invention exhibit excellent neuroleptic activity. This invention is based on the above finding.

Accordingly, a main object of the present invention is to provide the imide derivatives (I) and their salts. Another obejct of this invention is to provide processes for production of the imide derivatives (I) and their salts. A further object of the invention is to provide the use of the imide derivatives (I) and their salts as antipsychotic drugs, particularly neuroleptics.

The imide derivatives (I) of the invention can be produced by various processes, of which typical examples are set forth below.

Process (A):

The imide derivative (I) is obtainable by either one of the following reactions:

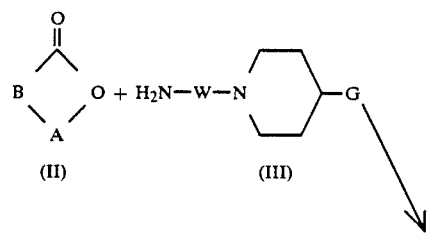

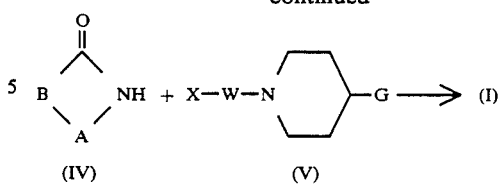

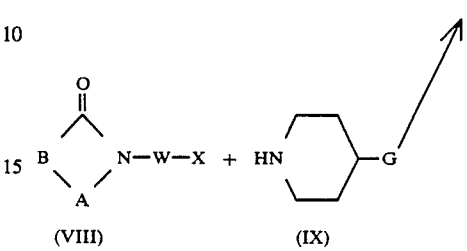

wherein A, B, G and W are each as defined above and X is a leaving group such as a halogen atom (e.g. chlorine, bromine, iodine), an alkylsulfonyloxy group (e.g. methanesulfonyloxy) or an arylsulfonyloxy group (e.g. p-toluenesulfonyloxy).

The imide derivative (I) can be prepared by reacting the compound (II) with the amine (III) in an inert solvent (e.g. pyridine, n-butanol, benzene, toluene, xylene), preferably under reflux.

The imide derivative (I) can be also prepared by reacting the compound (IV) with the compound (V) in an inert solvent (e.g. benzene, toluene, xylene, dimethylformamide, acetonitrile, n-butanol) in the presence of an acid binding agent such as a carbonate, bicarbonate or hydride of an alkali or alkaline earth metal (e.g. potassium carbonate, sodium bicarbonate, sodium hydride), a tertiary amine (e.g. triethylamine) or a pyridine base (e.g. pyridine), usually at room temperature or under heating.

The imide derivative (I) can be further prepared by reacting the compound (VIII) with an amine (IX) in an inert solvent (e.g. benzene, toluene, xylene, dimethylformamide, acetonitrile, n-butanol) in the presence of an acid binding agent such as a carbonate, bicarbonate or hydride of an alkali or alkaline earth metal (e.g. potassium carbonate, sodium bicarbonate, sodium hydride), a tertiary amine (e.g. triethylamine) or a pyridine base (e.g. pyridine), usually at room temperature or under heating.

The starting compounds (II), (III), (IV), (V), (VIII) and (IX) are per se known or can be produced by known methods, of which some examples are shown below.

(i) Compound (II):

The compound (II) is described in the following literatures or may be obtainable by the methods as disclosed therein: Japanese Pat. Publn. (unexamined) No. 87262/1985; J.Am.Chem.Soc., 63, 3167 (1941); J.Am.Chem.Soc., 72, 1678 (1950); J.Am.Chem.Soc., 74, 3094 (1952); J.Am.Chem.Soc., 73, 4889 (1951); Justus Liebigs Annalen der Chemie, 514, 1 (1934), etc.

(ii) Compounds (IV) and (VIII):

The compounds (IV) and (VIII) are obtainable according to the following formulas:

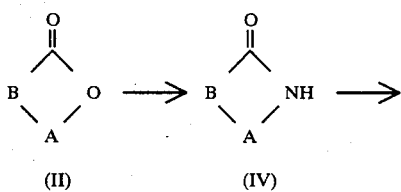

(II) → (IV) →

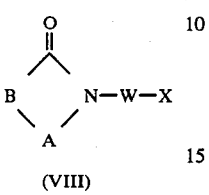

(VIII)

wherein A, B, W and X are each as defined above.

Namely, the compound (VIII) is produced from the compound (II) through the compound (IV) in a manner as described in EP-A No. 0109562, JP-A No. 87262/1985, JP-A No. 87284/1985, JP-A No. 23373/1985, etc.

(iii) Compounds (III), (V) and (IX):

These compounds are know or can be prepared by known methods. For instance, the compound (IX) is disclosed in JP-A No. 227882/1986 or can be prepared by the method as described therein. Further, the compounds (III) and (V) are obtainable according to the following schemes

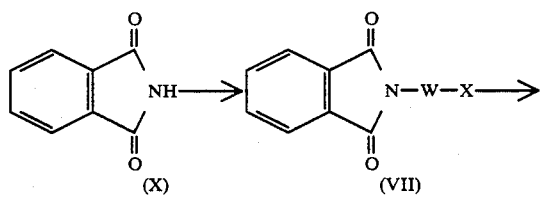

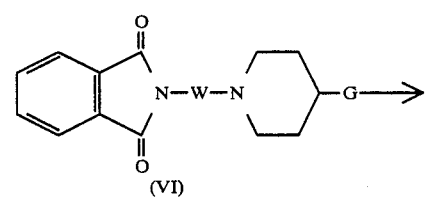

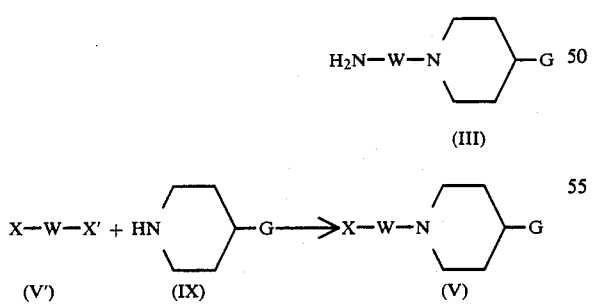

wherein G, W and X are each as defined above and X' is a leaving group such as a halogen atom, an alkylsulfonyloxy group or an arylsulfonyloxy group.

Namely, the compound (III) is obtainable by converting phthalimide (X) into the compound (VI) in the compound (VII) in a manner as disclosed in JP-A No. 87262/1985 and then convering the compound (VI) into the compound (III) by a Gabriel reaction. The compound (V) is obtainable by reacting the compound (V') with the compound (IX).

Process (B):

The imide derivative (I-1: W=lower alkylene) is obtainable by the following reaction:

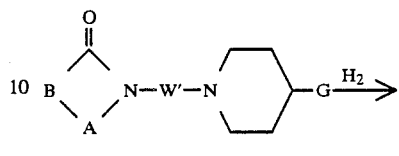

(XI)

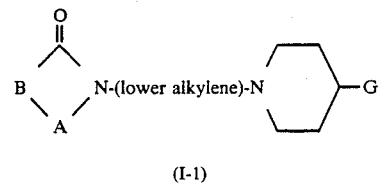

(I-1)

wherein A, B and G are each as defined above and W' is a lower alkenylene group or a lower alkynylene group.

Namely, the compound (I-1) is prepared by hydrogenation of the compound (XI). The hydrogenation may be achieved by any per se conventional procedure, particularly catalytic reduction. The catalytic reduction is usually carried out by treatment with hydrogen in the presence of a catalyst such as a metal (e.g. platinium, palladium, rhodium, nickel, cobalt), optionally deposited on a carrier such as carbon in an inert solvent (e.g. benzene, toluene, hexane, methanol, ethanol, ether, tetrahydrofuran, dioxane, ethyl acetate) at an ordinary temperature under an ordinary pressure. When desired, heating or cooling as well as elevation of pressure may be adopted for regulation of the reaction. After a theoretical amount of hydrogen is absorbed, the reaction mixture may be subjected to post-treatment in a conventional manner to recover the reaction product, which may be optionally purified.

The starting compound (XI) may be produced through Process (A) as hereinabove described or through Process (C) or (D) as hereinafter explained.

Process (C):

The imide derivative (I-2: W=—CH$_2$C≡CCH$_2$—) is obtainable by the following reaction:

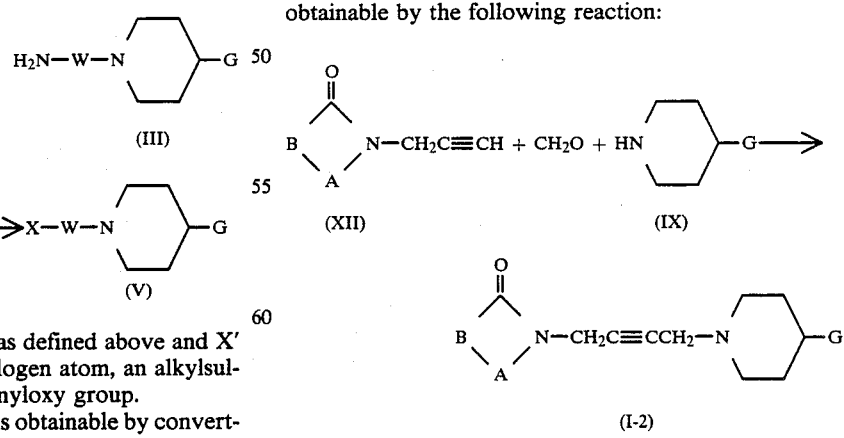

(I-2)

wherein A, B and G are each as defined above.

Namely, the N-propargyl derivative (XIII) is reacted with the piperazine derivative (IX) and formaldehyde in an inert solvent according to the Mannich reaction to produce the compound (I-2). In the reaction system, the presence of a metallic ion as a catalyst is preferred to accomplish the reaction smoothly; a metal salt such as copper chloride, copper sulfate, copper acetate or iron chloride may be thus incorporated into the reaction system. Examples of the inert solvent are water, dioxane, tetrahydrofuran, ether, methylene glycol dimethyl ehter, methyl cellosolve, etc. When desired, heating or cooling may be adopted for regulation of the reaction.

The starting compounds (XII) and (IX) may be produced through Process (A) as hereinabove described.

Process (D):

The imide derivative (I-3: W=lower alkenylene) is obtainable by the following reaction:

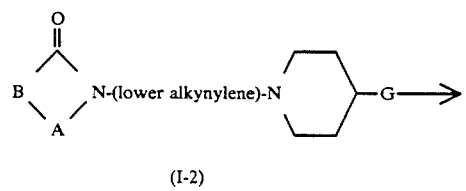

(I-2)

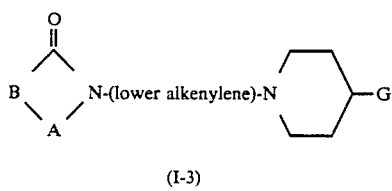

(I-3)

wherein A, B and G are each as defined above.

Namely, the compound (I-2) is subjected to hydrogenation, particularly catalytic hydrogenation to give the compound (I-3). The catalytic hydrogenation may be accomplished by treatment with hydrogen in the presence of a catalyst (e.g. platinium, palladium, rhodium, nickel, cobalt) in an inert solvent. For achievement of the hydrogenation partially, the use of a catalyst having a relatively weak activity such as palladium-calcium carbonate, palladium-barium sulfate or a Lindlar's catalyst, optionally poisoned with a basic amine, a sulfur compound or a copper compound is generally preferred. Examples of the inert solvent are benzene, toluene, hexane, methanol, ethanol, ether, tetrahydrofuran, ethyl acetate, etc. The reaction can proceed well at an ordinary temperature under an ordinary pressure, but heating or cooling as well as elevation of pressure may be adopted for regulation of the reaction, if necessary. After absorption of hydrogen in a theoretical amount, the reaction is terminated, and the reaction mixture may be subjected to post-treatment by a conventional procedure.

The starting compound (I-2) is prepared by either Process (A) or (C).

Process (E):

The imide derivative (I-4 or I-4': W=hydroxy-substituted lower alkylene) is obtainable by either one of the following reactions:

Procedure (1)

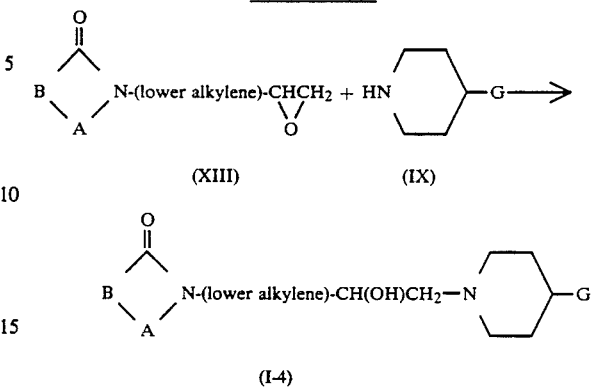

wherein A, B and G are each as defined above.

Namely, the epoxide (XIII) is reacted with the amine (IX) in an inert solvent, preferably under reflux, to give the compound (I-4). As the inert solvent, there may be exemplified benzene, toluene, xylene, dimethylformamide, acetonitrile, n-butanol, etc.

The starting compounds (XIII) and (IX) can be synthesized in the manner as described in Process (A).

Procedure (2)

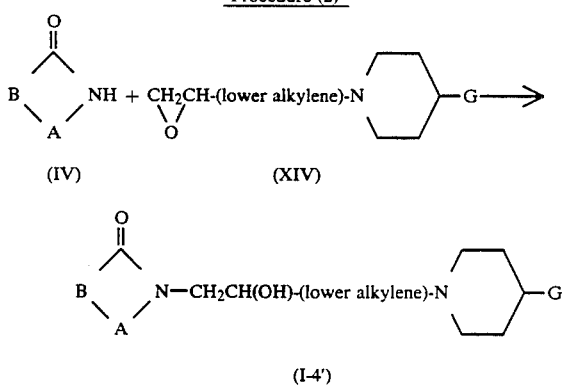

wherein A, B and G are each as defined above.

The compound (I-4') is prepared by reacting the compound (IV) with the amine (XIV) in an inert solvent in the presence of a base, usually at a room temperature or while heating. Examples of the inert solvent are benzene, toluene, xylene, dimethylformamide, acetonitrile, n-butanol, etc. As the base, there may be used a carbonate, bicarbonate or hydride of an alkali or alkaline earth metal (e.g. potassium carbonate, sodium bicarbonate, sodium hydride), a tertiary amine (e.g. triethylamine), a pyridine base (e.g. pyridine) or the like.

The starting compounds (IV) and (XIV) may be produced by Process (A).

As stated above, the imide derivatives (I) of the invention exert a significant neuroleptic activity. However, they show only a very weak extrapyramidal activity which is a typical side effect as generally observed in conventional neuroleptic drugs of the butyrophenone series and the phenothiazine series. In addition, it may be noted that the neuroleptic activity of conventional spiroimide compounds is remarkably reduced when administered orally, while that of the imide derivatives (I) is kept significant even when administered orally.

The above facts are well evidenced by the pharmacological test data as set forth below.

Test method

(1) Neuroleptic activity

This activity was examined through the anti-climbing behavior test, i.e. the test for suppressing the climbing behavior induced by apomorphine in mice. A designated amount of the test compound was orally administered to several groups of dd strain male mice (bodyweight, 20 to 25 g; one group, 5 mice), and each of the animals was charged in an individual column cage of 12 cm in diameter and 14 cm in height having metal poles (each pole, 2 mm in diameter) vertically installed and arranged along the periphery with intervals of 1 cm. After 50 minutes, apomorphine (1.0 mg/kg) was subcutaneously injected, and 10 minutes after the injection, the behavior was observed during 10 minutes. An evaluation was made on the basis of the following criteria [P. Protais et al.: Psychopharmacology, 50, 1-6 (1976)]:

| Score | Evaluation |
| --- | --- |
| 0 | All the paws were on the floor |
| 1 | Only forepaws seized the pole of the cage |
| 2 | All the paws seized the pole of the cage; climbing behavior observed discontinuously |
| 3 | Continuous climbing behavior observed |

Clibming behavior control percentage per each dose was calculated by the following equation, and $ED_{50}$ (50% effective dose) was determined thereon:

$$\text{Control percentage (\%)} = \frac{\text{Total score in control group} - \text{Total score in tested group}}{\text{Total score in control group}} \times 100$$

The results are shown in Table 1.

(2) Extrapyramidal activity

This activity was examined through the catalepsy inducing activity test as described in M. Fujiwara et al.: Folia Formacol., Japon: 85, 259-274 (1985). A designated amount of the test compound was orally administered to dd strain male mice (bodyweight, 22 to 27 g), and 1 and 4 hours after the administration, catalepsy induction was checked according to the Wirth et al method. Thus, each of the animals was forced to hang its forepaws onto a metal pole of 2.5 mm in diameter horizontally situated at a height of 5 cm to keep in a strained state. The test was made with three repetitions, and the presence of at least one case in which the animal was kept in the strained state over a period of 30 seconds was deemed to have caused catalepsy.

The results are shown in Table 2.

TABLE 1

| Compound | $ED_{50}$ (mg/kg) | | |
| --- | --- | --- | --- |
| | Subcutaneous administration | Oral administration After 1 hour | After 4 hours |
| Compound No. 1 | 0.12 | 3.7 | 21.8 |
| Compound No. 2 | — | 3.5 | 3.4 |
| Compound No. 5 | <1 | 1.3 | 2.2 |
| Haloperidol | 0.21 | 0.67 | 0.44 |
| Tiaspiron | 0.23 | 9.4 | 61.5 |

TABLE 2

| Compound | $ED_{50}$ (mg/kg) |
| --- | --- |
| Compound No. 1 | 25-50 |
| Compound No. 2 | 10-30 |
| Compound No. 5 | 25 |
| Haloperidol | 3 |

From the above test results, it is understood that haloperidol used for comparison exhibits a significant neuroleptic activity (i.e. anti-climbing activity) but simultaneously exerts a considerably high level of extrapyramidal activity (i.e. catalepsy inducing activity). The imide derivatives (I) of the invention and tiaspiron show nearly the same significant level in neuroleptic activity when administered subcutaneously, but the activity of the former is much higher than that of the latter when administered orally. Further, the former enhances a strong neuroleptic activity after a lapse of 4 hours from the administration, so that it is clear that the activity is maintained. Furthermore, the extrapyramidal side effect of the imide derivatives (I) is much less than that of haloperidol. From these facts, it may be concluded that the imide derivatives (I) are neuroleptic drugs having a high selectivity and a high safety. Thus, the imide derivatives (I) are usable not only to ordinary patients for mental disorders but also to eldery patients who are apt to suffer from various side effects. It may be noted that some of the imide derivatives (I) exhibit not only neuroleptic activity but also other useful pharmacological activities such as analgesic activity, anti-allergic activity and circulatory activity.

For therapeutic administration, the imide derivatives (I) or their salts may be used in the form of conventional pharmaceutical preparations such as tablets, capsules, syrups, suspensions, solutions, emulsions and suppositories. Depending upon their administration route such as oral administration, parenteral administration or rectal administration, an appropriate preparation form may be used. In order to make these preparations, the imide derivatives (I) may be combined, if necessary, with suitable additives such as carriers, diluents, fillers, binders and stabilizers. In the case of an injection, pharmaceutically acceptable buffers, solubilizers, isotonizers, etc. may be incorporated therein.

While the dosage of the imide derivatives (I) may vary with the symptoms, the age and weight of the patient, the dosage form, the administration mode and the like, the imide derivatives (I) may be, in general, administered to adults in an amount of about 0.5 to 1000 mg, preferably of about 3 to 500 mg per day in a single dose or divided doses.

Practical and presently preferred embodiments for production of the compound (I) as well as the intermediary compounds thereto are illustratively shown in the following Examples and Reference Examples.

Production of the compound (II)

(II)

REFERENCE EXAMPLE 1 exo-5-Hydroxybicyclo[2.2.1]heptane-exo-cis-2,3-dicarboxylic acid

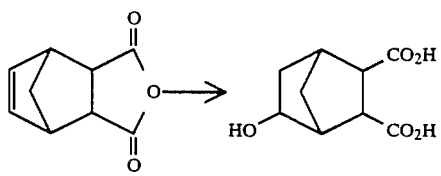

A suspension of bicyclo[2.2.1]hept-5-ene-exo-2,3-dicarboxylic anhydride (3 g) in 50% aqueous sulfuric acid (30 ml) was stirred at 80° C. for 3 hours and diluted with water (300 ml), followed by refluxing for 30 minutes. A slightly excess amount of aqueous barium chloride solution (a solution of barium chloride dihydrate (50 g) in water (200 ml)) was added thereto. After removal of the precipitated crystals by filtration, the filtrate was concentrated under reduced pressure. The residue was extracted with hot ethyl acetate (200 ml×2) and with hot acetone (300 ml×2). The extracts were combined together and concentrated under reduced pressure. The residual crystals were washed with acetonitrile to give the objective compound (1.09 g). Yield, 29.8%. M.P., 196°–198° C.

REFERENCE EXAMPLE 2 exo-5-Acetoxybicyclo[2.2.1]heptane-exo-2,3-dicarboxylic anhydride

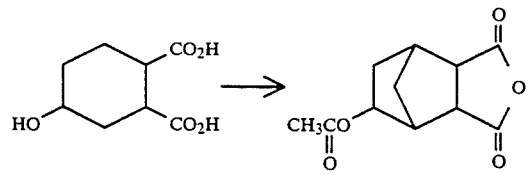

A mixture of exo-5-hydroxybicyclo[2.2.1]heptane-exo-2,3-dicarboxylic acid (3 g) and acetyl chloride (30 ml) was refluxed for 2 hours, followed by the removal of acetyl chloride under reduced pressure. The residue was combined with benzene, followed by distillation to give the objective compound as an oily substance.

Production of the compound (IV)

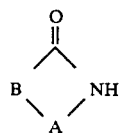
(IV)

REFERENCE EXAMPLE 3

Bicyclo[2.2.1]octane-2,3-dicarboximide

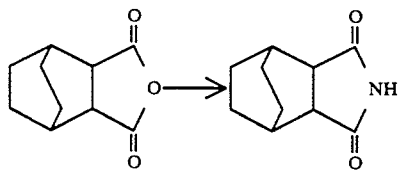

A solution of bicyclo[2.2.1]octane-2,3-dicarboxylic anhydride (3 g; 16.6 mmol) in tetrahydrofuran (9 ml) was dropwise added to a mixture of 29% aqueous ammonia (6 g; 83 mmol) and water (18 ml) while ice-cooling, and the resultant mixture was heated. After removal of the solvent by distillation under an ordinary pressure, acetic anhydride (10 ml) was added thereto, followed by refluxing for 30 minutes. The solvent was removed by distillation under reduced pressure, and the residue was combined with toluene (24 ml) and heated to dissolve. After cooling, the precipitated crystals were collected by filtration to give the objective compound. M.P., 199°–200° C.

REFERENCE EXAMPLE 4

Cyclohexane-1,2-dicarboximide

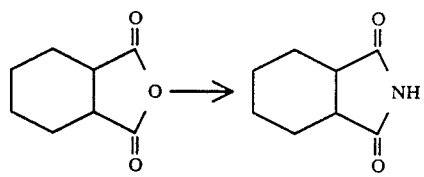

A mixture of cyclohexane-1,2-dicarboxylic anhydride (3 g; 19.5 mmol) and 29% aqueous ammonia (3.4 g) was heated to and kept at an inner temperature of 180° to 190° C. for 2 hours to give the objective compound quantitatively. M.P., 132°–136° C.

In the same manner as in Reference Example 3 or 4, the compounds as shown in Table 3 were obtained.

TABLE 3

| Structure | Physical property |
|---|---|
| bicyclo[2.2.2]octane dicarboximide | M.P., 153–155° C. |
| bicyclo[2.2.1]heptane dicarboximide | M.P., 173–176° C. |
| 4-methylcyclohexane dicarboximide | M.P., 75–82° C. |
| bicyclo[2.2.1]hept-5-ene dicarboximide | M.P., 187.5–189° C. |

TABLE 3-continued

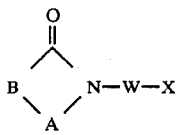

| | Physical property |
|---|---|
| 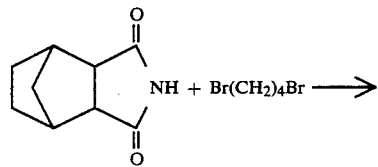 | M.P., 163.5–164.5° C. |

Production of the compound (VIII)

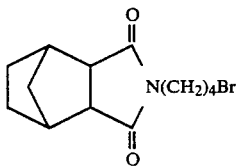 (VIII)

REFERENCE EXAMPLE 5

N-(4-Bromobutyl)bicyclo[2.2.1]heptane-2,3-di-exo-carboximide

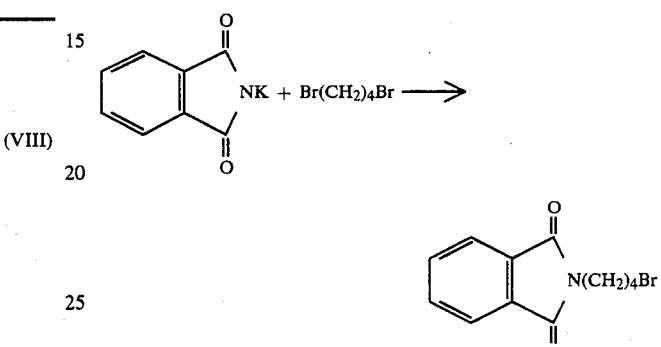

A mixture of bicyclo[2.2.1]heptane-2,3-di-exo-carboximide (50 g), tetramethylene dibromide (327 g), anhydrous potassium carbonate (50 g) and acetone (500 ml) was heated under reflux for 5 hours while stirring, followed by cooling. After removal of insoluble materials by filtration, the filtrate was distilled under reduced pressure to give the objective compound as an oily substance (71.4 g). Yield, 78.6%. b.p., 173°–180° C./0.04 mmHg. IR $\nu_{max}^{film}$ (cm$^{-1}$): 1765, 1700, 1430, 1395.

REFERENCE EXAMPLE 6

N-(4-Bromobutyl)phthalimide

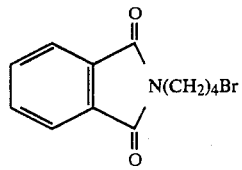

A mixture of phthalimide potassium salt (2 g; 10.8 mmol), 1,4-dibromobutane (10.8 g; 50 mmol) and dry dimethylformamide (10 ml) was stirred at a bath temperature of 90° to 100° C. for 10 hours. The precipitated crystals were removed by filtration, and the filtrate was concentrated under reduced pressure. Excess of 1,4-dibromobutane was removed by distillation, and the residue was purified by silica gel column chromatography to give the objective compound. M.P., 81°–82° C.

In the same manner as in Reference Example 5 or 6, the compounds as shown in Table 4 were obtained.

TABLE 4

| | W | X | Physical property |
|---|---|---|---|
| bicyclo[2.2.1]heptane-2,3-dicarboximide | —(CH$_2$)$_4$— | Br | IR $\nu_{max}^{film}$ (cm$^{-1}$): 1765, 1700 |
| bicyclo[2.2.1]hept-5-ene-2,3-dicarboximide | —(CH$_2$)$_4$— | Br | IR $\nu_{max}^{film}$ (cm$^{-1}$): 1770, 1700 |

TABLE 4-continued
| | W | X | Physical property |
|---|---|---|---|
| 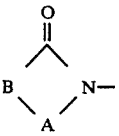 | —(CH$_2$)$_4$— | Br | b.p., 167–170° C./ 0.15 mmHg |
| 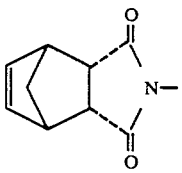 | —(CH$_2$)$_4$— | Br | IR $\nu_{max}^{film}$ (cm$^{-1}$): 1770, 1700 |
| 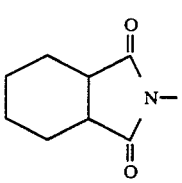 | —(CH$_2$)$_4$— | Br | IR $\nu_{max}^{film}$ (cm$^{-1}$): 1760, 1690 |
| 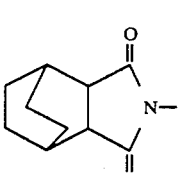 | —CH$_2$—C(H)=C(H)—CH$_2$— | Cl | IR $\nu_{max}^{film}$ (cm$^{-1}$): 1755, 1690 |
| 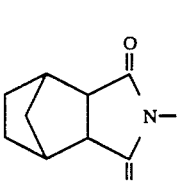 | —CH$_2$—C(H)=C(H)—CH$_2$— | Cl | IR $\nu_{max}^{film}$ (cm$^{-1}$): 1760, 1690 |
| 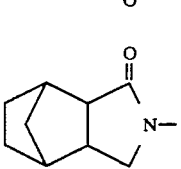 | —CH$_2$—C(H)=C(H)—CH$_2$— | Cl | IR $\nu_{max}^{film}$ (cm$^{-1}$): 1780, 1700 |
| 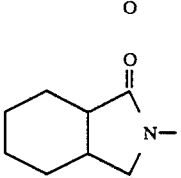 | —CH$_2$—C(H)=C(H)—CH$_2$— | Cl | IR $\nu_{max}^{film}$ (cm$^{-1}$): 1760, 1700 |
| 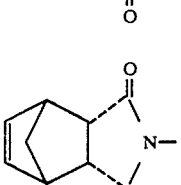 | —CH$_2$—C(H)=C(H)—CH$_2$— | Cl | IR $\nu_{max}^{film}$ (cm$^{-1}$): 1775, 1700 |

TABLE 4-continued

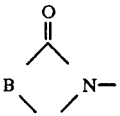

| A–B | W | X | Physical property |
|---|---|---|---|
| 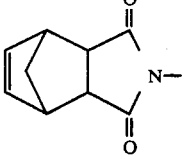 | —CH$_2$—C=C—CH$_2$— (H, H) | Cl | IR $\nu_{max}^{film}$ (cm$^{-1}$): 1765, 1705 |
| 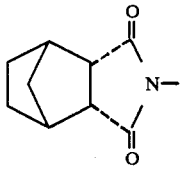 | —CH$_2$—C=C—CH$_2$— (H, H) | Cl | IR $\nu_{max}^{film}$ (cm$^{-1}$): 1760, 1700 |
| 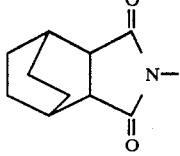 | —CH$_2$—C=C—CH$_2$— (H, H) | Cl | IR $\nu_{max}^{film}$ (cm$^{-1}$): 1760, 1685–1705 |
| 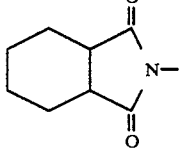 | —CH$_2$—C≡C—CH$_2$— | Cl | IR $\nu_{max}^{film}$ (cm$^{-1}$): 1780, 1700–1720 |

REFERENCE EXAMPLE 7

N-(4-Bromo-3-hydroxybutyl)cyclohexane-1,2-dicarboximide

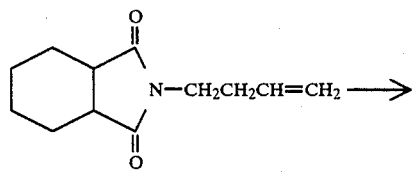

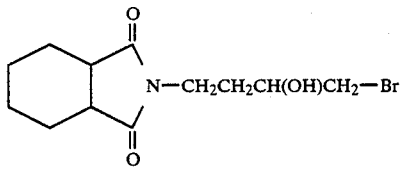

A mixture of N-(3-butenyl)cyclohexane-1,2-dicarboximide (1 g; 4.8 mmol), N-bromosuccinimide (0.86 g; 4.8 mmol) and water (2 ml) was stirred at room temperature for 4 hours. After completion of the reaction, water was added to the reaction mixture to dissolve insoluble materials, followed by extraction with benzene. The benzene extract was washed with a saturated aqueous sodium chloride solution, dried over magnesium sulfate and concentrated under reduced pressure to give the objective compound (1.4 g). Yield, 95.8%. IR $\nu_{max}^{film}$ (cm$^{-1}$): 1760, 1700, 1440, 1400, 1360.

Production of the compound (IX)

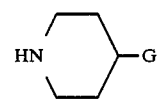

REFERENCE EXAMPLE 8

3-(4-Piperidinyl)-1,2-benzisothiazole (XIX)

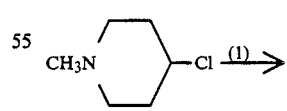

(XV)

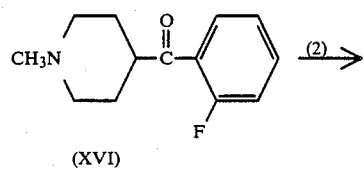

(XVI)

-continued

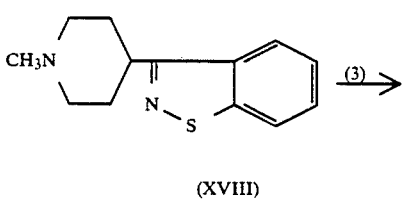

(XVIII)

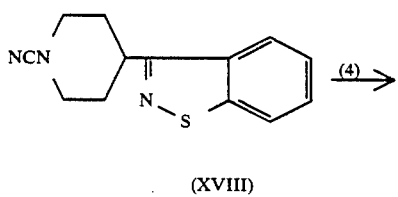

(XVIII)

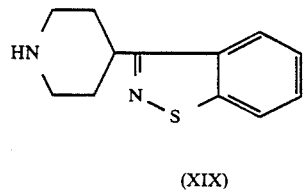

(XIX)

(1) To a mixture of magnesium chloride (12.1 g; 0.13 mol), naphthalene (3.3 g; 0.025 mol) and tetrahydrofuran (115 ml) was added metallic lithium (1.8 g) while stirring at room temperature, and stirring was continued at the same temperature for 23 hours. A solution of 4-chloro-N-methylpiperidine (17 g; 0.13 mol) in tetrahydrofuran (85 ml) was dropwise added thereto, followed by refluxing for 2 hours. Tetrahydrofuran was distilled under reduced pressure, and the residue was added to a solution of ammonium chloride (34 g; 0.64 mol) in ice-water (480 ml), followed by refluxing for 3 hours. After cooling, the reaction mixture was extracted with benzene (250 ml×3) and dried over magnesium sulfate, followed by distillation of the solvent. The residue was purified by silica gel column chromatography to give the compound (XVI) (4.8 g). Yield, 20.5%. A portion of this compound was treated with hydrogen chloride to give the hydrochloride. M.P., 158°-161° C.

(2) A solution of the compound (XVI) (4.8 g) and sulfur (0.86 g) in a saturated ammonia solution of ethylene glycol monomethyl ether (19.2 ml) was sealed and kept at 130° C. for 10 hours. After cooling, insoluble materials were eliminated by filtration, and the filtrate was concentrated under reduced pressure. The residue was purified by silica gel column chromatography to give the compound (XVII) (2.5 g). Yield, 50%. IR $\nu_{max}^{film}$ (cm$^{-1}$): 1485, 1450, 1380, 1345.

(3) To a mixture of the compound (XVII) (2.4 g; 10.3 mmol), potassium carbonate (1.9 g; 13.4 mmol) and chloroform (25 ml), cyanogen bromide (1.3 g; 12.4 mmol) was added while stirring at room temperature, followed by refluxing for 8 hours. Cyanogen bromide (0.67 g) was further added thereto, and the resultant mixture was refluxed for 2 hours. After cooling, insoluble materials were filtered off, and the filtrate was removed under reduced pressure. The residue was purified by silica gel column chromatography to give the compound (XVIII) (1.5 g). Yield, 59.7%. IR $\nu_{max}^{film}$ (cm$^{-1}$): 2210, 1590, 1475, 1460, 1440.

(4) A mixture of the compound (XVIII) (1.5 g) and 25% aqueous sulfuric acid (15 ml) was refluxed for 15.5 hours. After cooling, the resultant mixture was poured into ice-water, neutralized with sodium hydroxide and extracted with dichloromethane. The extract was washed with a saturated aqueous sodium chloride solution, dried over magnesium sulfate and concentrated under reduced pressure. The residue was purified by silica gel column chromatography to give the compound (XIX) (1.0 g). Yield, 74.3%. A portion of the compound was treated with hydrogen chloride to give the hydrochloride. M.P., 260° C.

REFERENCE EXAMPLE 9

4-(4-Fluorobenzoyl)piperidine (XXIII)

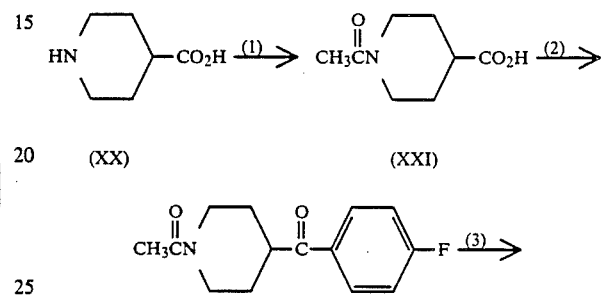

(1) A mixture of isonipecotinic acid (25.8 g; 0.2 mol) and acetic anhydride (100 ml) was refluxed for 2.5 hours, followed by distillation of the solvent under reduced pressure. The residue was crystallized from a mixture of ether and isopropyl ether to give the compound (XXI) (19 g). Yield, 62.9%. M.P., 163°-178° C. (crude crystals).

(2) To a solution of the compound (XXI) (18.1 g; 0.12 mol) in chloroform (180 ml), thionyl chloride (42.8 g; 0.36 mol) was added, and the resultant mixture was refluxed for 2 hours. After cooling, the precipitated crystals were collected by filtration to give the acid chloride (15.8 g). M.P., 130°-138° C. (crude crystals).

The acid chloride (15.3 g; 0.09 mol) was portionwise added to a mixture of aluminium chloride (25 g; 0.18 mol) and fluorobenzene (40 ml), followed by refluxing for 1 hour. After cooling, the reaction mixture was poured into ice-water (400 g) and extracted with chloroform. The extract was washed with water, dried over magnesium sulfate and concentrated under reduced pressure to give the compound (XXII) (14.7 g). Yield, 65.1%. IR $\nu_{max}^{film}$ (cm$^{-1}$): 1670, 1650, 1590, 1500, 1315.

(3) A mixture of the compound (XXII) (14.5 g; 0.058 mol) and 6N aqueous hydrochloric acid (44 ml) was refluxed for 2 hours, and after cooling, washed with ether. The aqueous layer was adjusted to pH 10 with addition of sodium hydroxide under cooling and extracted with chloroform. The extract was dried over sodium sulfate and concentrated under reduced pressure. The residue was washed with a mixture of isopropyl ether and n-butane to give the compound (XXIII) (8.8 g). Yield, 73.4%. M.P., 70°-72° C.

Production of the compound (XII)

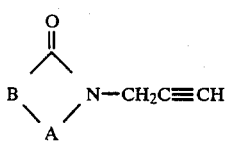
(XIII)

REFERENCE EXAMPLE 10

N-Propargylbicyclo[2.2.1]heptane-2,3-di-exo-carboximide

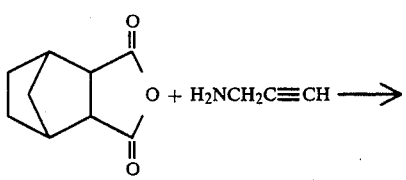

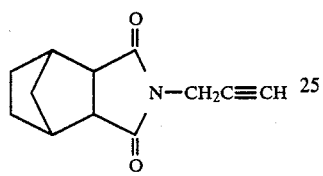

To a solution of propargylamine (1.12 g) in dry tetrahydrofuran (10 ml), a solution of bicyclo[2.2.1]heptane-2,3-di-exo-carboxylic anhydride (1.64 g) in dry tetrahydrofuran (10 ml) was dropwise added at room temperature under stirring, and the resultant mixture was gradually heated to distill off the solvent and kept at an oily bath temperature of 150° C. for 30 minutes. The residue was purified by chromatography to give the objective compound. Yield, 81%. M.P., 94°-94.5° C.

REFERENCE EXAMPLE 11

N-Propargylbicyclo[2.2.1]heptane-2,3-di-exo-carboximide

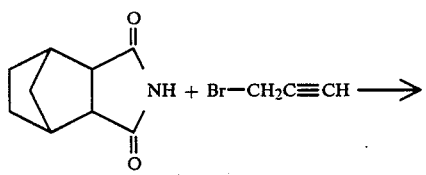

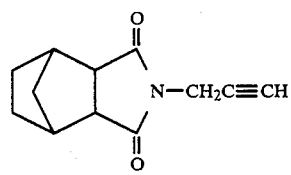

A solution of bicyclo[2.2.1]heptane-2,3-di-exo-carboximide (3.30 g), propargyl bromide (2.62 g) and anhydrous potassium carbonate (3.32 g) in dry acetone (30 ml) was stirred under reflux for 1 hour in a nitrogen atmosphere. After cooling, inorganic materials were removed by filtration, and the filtrate was concentrated under reduced pressure. The residue was combined with chloroform (20 ml) and n-hexane (20 ml), and insoluble materials were eliminated by filtration with celite. The filtrate was evaporated, and the residue was recrystallized from n-hexane to give the objective compound. Yield, 91%. M.P., 94°-94.5° C.

In the same manner as in Reference Example 10 or 11, the compounds as shown in Table 5 were obtained.

TABLE 5

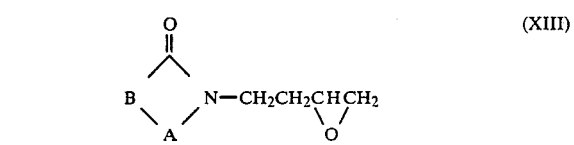

| | Physical property |
|---|---|
| (structure shown) | M.P., 124–126° C. |

Production of the compound (XIII)

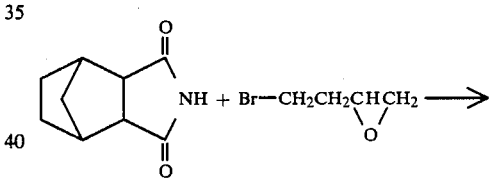
(XIII)

REFERENCE EXAMPLE 12

N-(3,4-Epoxybutyl)bicyclo[2.2.1]heptane-2,3-di-exo-carboximide

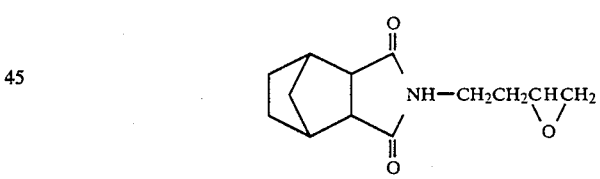

A mixture of bicyclo[2.2.1]heptane-2,3-di-exo-carboximide (2.3 g; 14.2 mmol), 4-bromo-1,2-epoxybutane (2 g; 14.2 mmol), potassium carbonate (2.9 g; 21.3 mmol) and acetone (35 ml) was stirred for 8.5 hours under reflux. After completion of the reaction, the reaction mixture was cooled, and insoluble materials were removed by filtration. The filtrate was concentrated under reduced pressure. The residue was combined with toluene (100 ml), and the resulting mixture was shaken with a saturated aqueous sodium chloride solution (50 ml). The aqueous layer was re-extracted with toluene (100 ml), and the toluene extract was combined with the organic layer, dried over magnesium sulfate and concentrated under reduced pressure. The residue was purified by silica gel column chromatography to give the objective compound (2.6 g). Yield, 79.4%. IR $\nu_{max}^{film}$ (cm$^{-1}$): 1765, 1700, 1480, 1440, 1400.

REFERENCE EXAMPLE 13

N-(3,4-Epoxybutyl)bicyclo[2.2.1]heptane-2,3-di-exo-carboximide

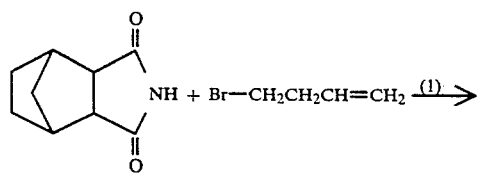

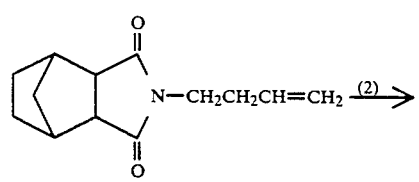

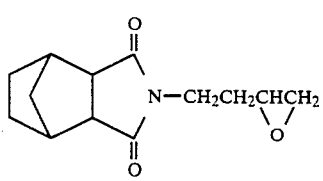

(1) To a mixture of bicyclo[2.2.1]heptane-2,3-di-exo-carboximide (1.65 g) and dimethylformamide (5 ml), a solution of 4-bromo-1-butene (1.62 g) in dimethylformamide (3 ml) was added while stirring at room temperature, followed by addition of powdery anhydrous potassium carbonate (2.07 g) thereto. The resultant mixture was heated and allowed to react at an inner temperature of 90° to 100° C. for 1 hour. The reaction mixture was combined with chloroform and subjected to filtration. The filtrate was concentrated under reduced pressure, combined with toluene, washed with water and dried. The solvent was removed under reduced pressure to give the objective compound (2.22 g) as an oily substance. IR $\nu_{max}^{film}$ (cm$^{-1}$): 3050, 3000, 2925, 1485, 1440.

(2) To a solution of N-(3-butenyl)bicyclo[2.2.1]-heptane-2,3-di-exo-carboximide (2.05 g) in dichloromethane (15 ml), a solution of m-chloroperbenzoic acid (2.4 g) in dichloromethane (35 ml) was added while stirring at room temperature, and the resultant mixture was allowed to react for 15 hours. After completion of the reaction, the reaction mixture was treated with an aqueous solution of sodium thiosulfate, washed with an aqueous solution of sodium bicarbonate and dried. The solvent was distilled under reduced pressure, and the residue was purified by silica gel column chromatography to give the objective compound (2.03 g) as an oily substance. IR $\nu_{max}^{film}$ (cm$^{-1}$): 1765, 1700, 1480, 1440, 1400.

In the same manner as in Reference Example 12 or 13, the compounds as shown in Table 6 were obtained.

TABLE 6

(XIII)

$$\text{B} \diagdown_{\text{A}}\!\!\diagup \text{N—CH}_2\text{CH}_2\text{CHCH}_2 \text{ (epoxide)}$$

with acyl groups on B/A

| $\text{B} \diagdown_{\text{A}}\!\!\diagup \text{N—}$ | Physical property |
|---|---|
| (norbornane diimide) | IR $\nu_{max}^{film}$ (cm$^{-1}$): 1770, 1700, 1440, 1400 |
| (cyclohexane-fused) | IR $\nu_{max}^{film}$ (cm$^{-1}$): 1775, 1710, 1445, 1405, 1355 |
| (methylcyclohexane-fused, H$_3$C—) | IR $\nu_{max}^{film}$ (cm$^{-1}$): 1765, 1700, 1440, 1395, 1350 |
| (norbornene diimide) | IR $\nu_{max}^{film}$ (cm$^{-1}$): 1765, 1705, 1440, 1395, 1365 |
| (cyclohexene-fused) | IR $\nu_{max}^{film}$ (cm$^{-1}$): 1770, 1700, 1440, 1400, 1365 |
| (bicyclic) | IR $\nu_{max}^{film}$ (cm$^{-1}$): 1765, 1680, 1440, 1405, 1390 |

Production of the compound (I)

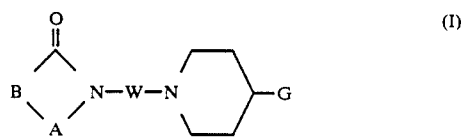

(I)

EXAMPLE 1

N-[4-{4-(4-Fluorobenzoyl)piperidinyl}butyl]bicyclo[2,2.1]heptane-2,3-di-exo-carboximide (Compound No. 1)

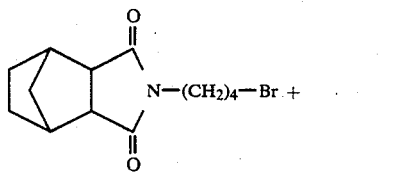

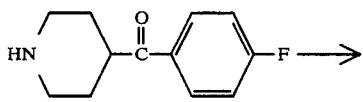

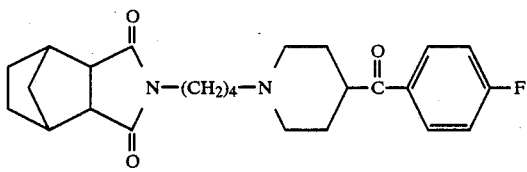

A mixture of N-(4-bromobutyl)bicyclo[2.2.1]heptane-2,3-di-exo-carboximide (1.92 g), 4-(4-fluorobenzoyl)-piperidine (1.2 g), sodium carbonate (0.68 g) and dimethylformamide (30 ml) was kept at 100° C. for 3 hours. After being allowed to cool, the resultant mixture was added to water (200 ml). The precipitated crystals were collected by filtration, washed with water and recrystallized from a mixture of isopropanol and isopropyl ether to give the objective compound (1.53 g). Yield, 61.9%. M.P., 130°–131° C.

EXAMPLE 2

N-[4-{4-(1,2-Benzisothiazol-3-yl)-1-piperidinyl}butyl]-bicyclo[2.2.1]heptane-2,3-di-exo-carboximide (Compound No. 2)

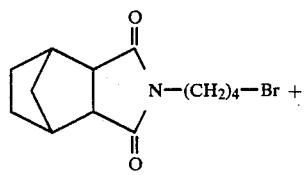

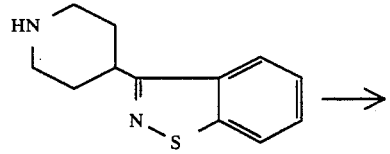

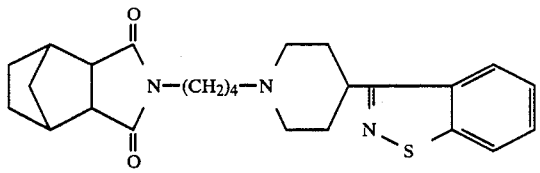

A mixture of 3-(4-piperidinyl)-1,2-benzisothiazole (0.8 g), N-(4-bromobutyl)bicyclo[2.2.1]heptane-2,3-di-exo-carboximide (1.3 g), potassium carbonate (0.6 g), potassium iodide (73 mg) and dimethylformamide (16 ml) was kept at 90° to 100° C. for 3 hours. After being allowed to cool, the reaction mixture was added to water and extracted with chloroform. The chroloform extract was concentrated under reduced pressure, and the residue was purified by silica gel column chromatography, followed by treatment with hydrogen chloride to give the objective compound (1.12 g). Yield, 64.5%. M.P., 231°–233° C. (HCl salt).

EXAMPLE 3

N-[4-{4-(4-Fluorobenzoyl)piperidinyl}-2-hydroxybutyl]cyclohexane-1,2-dicarboximide (Compound No. 3)

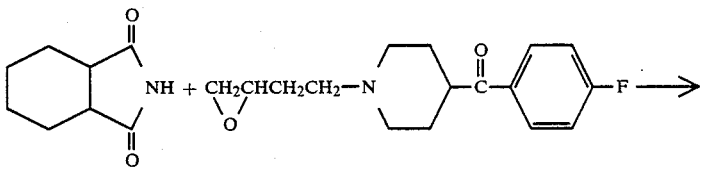

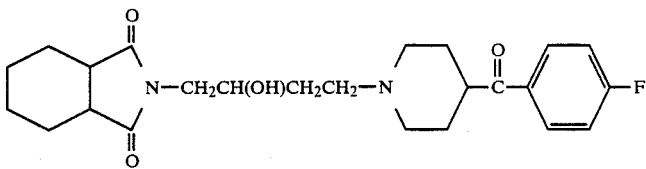

To a mixture of 60% sodium hydride (0.26 g) and dimethylformamide (20 ml), cyclohexane-1,2-dicarboximide (1.13 g) was gradually added. A mixture of 1-(3,4-epoxybutyl)-4-(4-fluorobenzoyl)piperidine (1.7 g) and dimethylformamide (50 ml) was dropwise added thereto at room temperature, and the resultant mixture was kept at an inner temperature of 90° to 100° C. for 3 hours. Insoluble materials were removed by filtration, and the filtrate was distilled to eliminate dimethylformamide. The residue was dissolved in chloroform, washed with water, dried over magnesium sulfate and concentrated under reduced pressure. The residue was purified by silica gel column chromatography to give the objective compound (0.27 g). Yield, 10.2%. M.P., 129°–130° C.

EXAMPLE 4

N-[4-{4-(4-Fluorobenzoyl)piperidinyl}-3-hydroxybutyl]cyclohexane-1,2-dicarboximide (Compound No. 4)

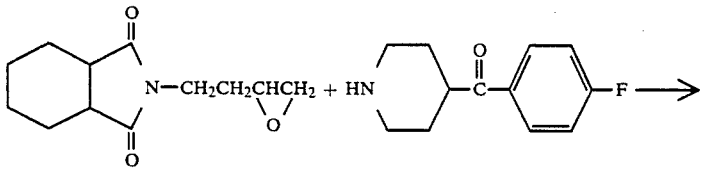

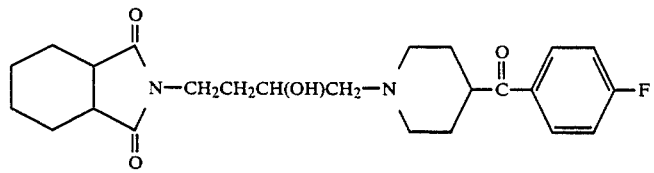

A mixture of N-(3,4-epoxybutyl)cyclohexane-1,2-dicarboximide (3 g), 4-(4-fluorobenzoyl)piperidine (3.23 g) and n-butanol (62 ml) was refluxed for 6 hours, followed by evaporation of n-butanol under reduced pressure. The residue was purified by silica gel column chromatography to give the objective compound (2.3 g). Yield, 38.2%. M.P., 121°–122° C.

EXAMPLES 5 to 50

In the same manner as in Example 1, 2, 3 or 4, there were obtained the following compounds:

N-[4-{4-(4-Fluorobenzoyl)piperidinyl}butyl]bicyclo[2.2.1]hept-5-ene-2,3-di-exo-carboximide (Compound No. 5). M.P., 125°–127° C.

N-[4-{4-(4-Fluorobenzoyl)piperidinyl}-2-transbutenyl]bicyclo[2.2.1]heptane-2,3-di-exo-carboximide (Compound No. 6). M.P., 110°–111° C.

N-[4-{4-(4-Fluorobenzoyl)piperidinyl}butyl]cyclohexane-1,2-dicarboximide (Compound No. 7). M.P., 74°–76° C.

N-[4-{4-(4-Fluorobenzoyl)piperidinyl}butyl]-4-cyclohexene-1,2-dicarboximide (Compound No. 8). M.P., 93°–95° C.

N-[4-{4-(4-Fluorobenzoyl)piperidinyl}butyl]-4-methylcyclohexene-1,2-dicarboximide (Compound No. 9). M.P., 185°–187° C. (hydrochloride).

N-[4-{4-(4-Fluorobenzoyl)piperidinyl}butyl]bicyclo[2.2.1]heptane-2,3-di-endo-carboximide (Compound No. 10). M.P., 111°–112° C.

N-[4-{4-(4-Fluorobenzoyl)piperidinyl}-2-transbutenyl]-cyclohexane-1,2-di-carboximide (Compound No. 11). M.P., 201°–202° C. (hydrochloride).

N-[4-{4-(4-Fluorobenzoyl)piperidinyl}butyl]bicyclo[2.2.1]hepta-5-ene-2,3-di-endo-carboximide (Compound No. 12). M.P., 213°–214° C. (hydrochloride).

N-[4-{4-(4-Fluorobenzoyl)piperidinyl}-4-methylbutyl]bicyclo[2.2.1]heptane-2,3-di-exo-carboximide (Compound No. 13). M.P., 116°–117° C.

N-[4-{4-[(4-Fluorophenyl)hydroxymethyl]piperidinyl}butyl]bicyclo[2.2.1]hetane-2,3-di-exo-carboximide (Compound No. 14). IR $\nu_{max}^{film}$ (cm$^{-1}$): 1760, 1680.

N-[4-{4-[(4-Fluorophenyl)acetoxymethyl]piperidinyl}butyl]bicyclo[2.2.1]hetane-2,3-di-exo-carboximide (Compound No. 15). M.P., 188°–189° C. (hydrochloride).

N-[4-{4-(4-Fluorobenzyl)piperidinyl}butyl]bicyclo[2.2.1]hetane-2,3-di-exo-carboximide (Compound No. 16). M.P., 228°–229° C. (hydrochloride).

N-[4-{4-(4-Fluorobenzyl)piperidinyl}butyl]cyclohexane-1,2-dicarboximide (Compound No. 17). M.P., 187°–188° C. (hydrochloride).

N-[4-{4-[(4-Fluorophenyl)sulfonyl]piperidinyl}butyl]cyclohexane-1,2-dicarboximide (Compound No. 18). M.P., 189°–190° C. (hydrochloride).

N-[4-{4-[(4-Fluorophenyl)sulfonyl]piperidinyl}butyl]bicyclo[2.2.1]heptane-2,3-di-exo-carboximide (Compound No. 19). M.P., 209°–211° C. (hydrochloride).

N-[4-{4-[(4-Fluorophenyl)thio]piperidinyl}butyl]bicyclo[2.2.1]heptane-2,3-di-exo-carboximide (Compound No. 20). M.P., 244°–246° C. (hydrochloride).

N-[4-{4-[(4-Fluorophenyl)thio]piperidinyl}butyl]cyclohexane-1,2-dicarboximide (Compound No. 21). M.P., 197°–198° C. (hydrochloride).

N-[4-{4-[(4-Fluorophenyl)methoxymethyl]piperidinyl}butyl]bicyclo[2.2.1]heptane-2,3-di-exo-carboximide (Compound No. 22). IR $\nu_{max}^{film}$ (cm$^{-1}$): 1760, 1690.

N-[4-{4-[(4-Fluorophenyl)methoxymethyl]piperidinyl}butyl]cyclohexane-1,2-dicarboximide (Compound No. 23). IR $\nu_{max}^{film}$ (cm$^{-1}$): 1765, 1700.

N-[4-{4-[(4-Fluorophenyl)sulfinyl]piperidinyl}butyl]bicyclo[2.2.1]heptane-2,3-di-exo-carboximide (Compound No. 24). M.P., 197°–198° C. (hydrochloride).

N-[4-{4-(4-Fluorophenoxy)piperidinyl}butyl]bicyclo[2.2.1]heptane-2,3-di-exo-carboximide (Compound No. 25). M.P., 207°–209° C. (hydrochloride).

N-[4-{4-(4-Fluorophenoxy)piperidinyl}butyl]cyclohexane-1,2-dicarboximide (Compound No. 26). M.P., 199°–200° C. (hydrochloride).

N-[4-{4-[(4-Fluorophenyl)sulfinyl]piperidinyl}butyl]cyclohexane-1,2-dicarboximide (Compound No. 27). M.P., 181°–182° C. (hydrochloride).

8-[4-{4-(4-Fluorobenzoyl)piperidinyl}butyl]-8-azabispiro[4.5]decane-7,9-dione. (Compound No. 28). M.P., 226°–229° C. (hydrochloride).

2-[4-{4-(4-Fluorobenzoyl)piperidinyl}butyl]-1,2-benzisothiazole-3(2H)-one-1,1-dioxide (Compound No. 29). M.P., 226°–229° C. (hydrochloride).

N-[2-{4-(4-Fluorobenzoyl)piperidinyl}ethyl]cyclohexane-1,2-dicarboximide (Compound No. 30). M.P., 236°–240° C. (hydrochloride).

N-[5-{4-(4-Fluorobenzoyl)piperidinyl}pentyl]cyclohexane-1,2-dicarboximide (Compound No. 31). M.P., 196°–198° C. (hydrochloride).

1-[4-{4-(4-Fluorobenzoyl)piperidinyl}butyl]-4,4-dimethyl-2,6-piperidine-dione (Compound No. 32). M.P., 238°–240° C. (hydrochloride).

N-[3-{4-(4-Fluorobenzoyl)piperidinyl}propyl]cyclohexane-1,2-dicarboximide. (Compound No. 33). M.P., 239°-241° C. (hydrochloride).

N-[4-{4-(4-Fluorobenzoyl)piperidinyl}butyl]bicyclo[2.2.1]octane-2,3-dicarboximide. (Compound No. 34). M.P., 254°-255° C. (hydrochloride).

N-[4-{4-(4-Fluorobenzoyl)piperidinyl}butyl]-7-oxabicyclo[2.2.1]heptane-2,3-di-exo-carboximide. (Compound No. 35). M.P., 230°-231.5° C. (hydrochloride).

N-[4-{4-(4-Fluorobenzoyl)piperidinyl}methyl]cyclohexane-1,2-dicarboximide. (Compound No. 36). M.P., 160°-163° C. (hydrochloride).

N-[4-{4-(4-Methylbenzoyl)piperidinyl}butyl]bicyclo[2.2.1]heptane-2,3-di-exo-carboximide. (Compound No. 37). M.P., 117°-118° C.

N-[4-(4-Benzoylpiperidinyl)butyl]bicyclo[2.2.1]heptane-2,3-di-exo-carboximide. (Compound No. 38). M.P., 102°-103° C.

N-[4-{4-(4-Bromobenzoyl)piperidinyl}butyl]bicyclo[2.2.1]heptane-2,3-di-exo-carboximide. (Compound No. 39). M.P., 147°-147.5° C.

N-[4-{4-(4-Methoxybenzoyl)piperidinyl}butyl]bicyclo[2.2.1]heptane-2,3-di-exo-carboximide. (Compound No. 40). M.P., 120°-121° C.

N-[4-{4-[(4-Fluorophenyl)hydroxyiminomethyl]piperidinyl}butyl]bicyclo[2.2.1]heptane-2,3-di-exo-carboximide. (Compound No. 41; stereo isomer of Compound No. 42). M.P., 207°-207.5° C. (hydrochloride).

N-[4-{4-[(4-Fluorophenyl)hydroxyiminomethyl]piperidinyl}butyl]bicyclo[2.2.1]heptane-2,3-di-exo-carboximide. (Compound No. 42; stereo isomer of Compound No. 41). M.P., 220.5°-221° C. (hydrochloride).

N-[4-{4-(4-Fluorobenzoyl)piperidinyl}-2-hydroxybutyl]bicyclo[2.2.1]heptane-2,3-di-exo-carboximide. (Compound No. 43). M.P., 138°-140° C.

N-[4-{4-(4-Fluorobenzoyl)piperidinyl}-3-hydroxybutyl]bicyclo[2.2.1]hept-5-ene-2,3-di-endo-carboximide. (Compound No. 44). M.P., 112°-114° C.

N-[4-{4-(4-Fluorobenzoyl)piperidinyl}-3-hydroxybutyl]bicyclo[2.2.1]heptane-2,3-di-exo-carboximide. (Compound No. 45). M.P., 171°-172° C.

N-[4-{4-(1,2-Benzisothiazol-3-yl)piperidinyl}cyclohexane-1,2-dicarboximide. (Compound No. 46). M.P., 216°-217° C. (hydrochloride).

N-[4-{4-(1,2-Benzisothiazol-3-yl)piperidinyl}bicyclo[2.2.1]hepta-5-ene-2,3-di-exo-carboximide. (Compound No. 47). M.P., 226°-228° C. (hydrochloride).

N-[4-{4-(1,2-Benzisothiazol-3-yl)piperidinyl}bicyclo[2.2.2]octane-2,3-dicarboximide. (Compound No. 48). M.P., 213°-215° C. (hydrochloride).

N-[4-{4-(1,2-Benzisothiazol-3-yl)piperidinyl}bicyclo[2.2.1]heptane-2,3-di-endo-carboximide. (Compound No. 49). M.P., 224°-226° C. (hydrochloride).

N-[4-{4-(1,2-Benzisothiazol-3-yl)piperidinyl}-8-azabispiro[4.5]decane-7,9-dione (Compound No. 50). M.P., 197°-199° C. (hydrochloride).

The imide derivatives (I) as produced in Examples 1 to 50 are shown in Table 7.

TABLE 7

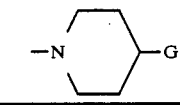

| Compound No. | 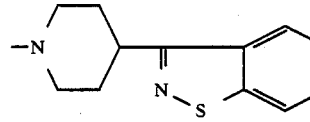 | —W— | 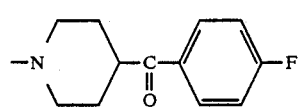 | Physical property |
|---|---|---|---|---|
| 1 | ![norbornane imide] | —(CH$_2$)$_4$— | ![piperidinyl-C(O)-C$_6$H$_4$-F] | M.P. 130–131° C. |
| 2 | ![norbornane imide] | —(CH$_2$)$_4$— | ![piperidinyl-benzisothiazole] | M.P. 231–233° C. (HCl) |
| 3 | ![cyclohexane imide] | —CH$_2$CH(OH)CH$_2$CH$_2$— | ![piperidinyl-C(O)-C$_6$H$_4$-F] | M.P. 129–130° C. |

TABLE 7-continued

Structure (I):

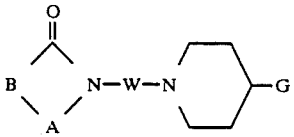

| Compound No. | B-A (ring) | —W— | piperidine-G | Physical property |
|---|---|---|---|---|
| 4 | cis-hexahydrophthalimide | —CH₂CH₂CH(OH)CH₂— | 4-(4-fluorobenzoyl)piperidine | M.P. 121–122° C. |
| 5 | 5-norbornene-2,3-dicarboximide | —(CH₂)₄— | 4-(4-fluorobenzoyl)piperidine | M.P. 125–127° C. |
| 6 | norbornane-2,3-dicarboximide | —CH₂CH=CHCH₂— (trans) | 4-(4-fluorobenzoyl)piperidine | M.P. 110–111° C. |
| 7 | cis-hexahydrophthalimide | —(CH₂)₄— | 4-(4-fluorobenzoyl)piperidine | M.P. 74–76° C. |
| 8 | 4-tetrahydrophthalimide | —(CH₂)₄— | 4-(4-fluorobenzoyl)piperidine | M.P. 93–95° C. |
| 9 | 4-methyl-4-tetrahydrophthalimide | —(CH₂)₄— | 4-(4-fluorobenzoyl)piperidine | M.P. 185–187° C. (HCl) |
| 10 | norbornane-2,3-dicarboximide | —(CH₂)₄— | 4-(4-fluorobenzoyl)piperidine | M.P. 111–112° C. |

TABLE 7-continued

| Compound No. | B⟨A⟩N— (with C=O) | —W— | —N⟨piperidine⟩G | Physical property |
|---|---|---|---|---|
| 11 | cyclohexane-fused succinimide (N—) | —CH₂CH=CHCH₂— (trans) | 4-(4-fluorobenzoyl)piperidine | M.P. 201–202° C. (HCl) |
| 12 | norbornene-fused succinimide (N—) | —(CH₂)₄— | 4-(4-fluorobenzoyl)piperidine | M.P. 213–214° C. (HCl) |
| 13 | norbornane-fused succinimide (N—) | —(CH₂)₃CH(CH₃)— | 4-(4-fluorobenzoyl)piperidine | M.P. 116–117° C. |
| 14 | norbornane-fused succinimide (N—) | —(CH₂)₄— | 4-[(4-fluorophenyl)(hydroxy)methyl]piperidine | IR $\nu_{max}^{film}$ (cm$^{-1}$): 1760, 1680 |
| 15 | norbornane-fused succinimide (N—) | —(CH₂)₄— | 4-[(4-fluorophenyl)(acetoxy)methyl]piperidine | M.P. 188–189° C. (HCl) |
| 16 | norbornane-fused succinimide (N—) | —(CH₂)₄— | 4-(4-fluorobenzyl)piperidine | M.P. 228–229° C. (HCl) |
| 17 | cyclohexane-fused succinimide (N—) | —(CH₂)₄— | 4-(4-fluorobenzyl)piperidine | M.P. 187–188° C. (HCl) |

TABLE 7-continued

Structure (I):

B–A–N–W–N(piperidine-4-G) with C=O on the N-W side

| Compound No. | B\A /N— (with A, B and C=O, forming imide) | —W— | —N⟨piperidine⟩—G | Physical property |
|---|---|---|---|---|
| 18 | cis-hexahydrophthalimide (cyclohexane-fused succinimide) | —(CH$_2$)$_4$— | 4-(4-fluorophenylsulfonyl)piperidin-1-yl (–SO$_2$–C$_6$H$_4$–F) | M.P. 189–190° C. (HCl) |
| 19 | norbornane-fused dicarboximide | —(CH$_2$)$_4$— | 4-(4-fluorophenylsulfonyl)piperidin-1-yl (–SO$_2$–C$_6$H$_4$–F) | M.P. 209–211° C. (HCl) |
| 20 | norbornane-fused dicarboximide | —(CH$_2$)$_4$— | 4-(4-fluorophenylthio)piperidin-1-yl (–S–C$_6$H$_4$–F) | M.P. 244–246° C. (HCl) |
| 21 | cis-hexahydrophthalimide | —(CH$_2$)$_4$— | 4-(4-fluorophenylthio)piperidin-1-yl (–S–C$_6$H$_4$–F) | M.P. 197–198° C. (HCl) |
| 22 | norbornane-fused dicarboximide | —(CH$_2$)$_4$— | 4-[(4-fluorophenyl)(methoxy)methyl]piperidin-1-yl (–CH(OCH$_3$)–C$_6$H$_4$–F) | IR $\nu_{max}^{film}$ (cm$^{-1}$): 1760, 1690 |
| 23 | cis-hexahydrophthalimide | —(CH$_2$)$_4$— | 4-[(4-fluorophenyl)(methoxy)methyl]piperidin-1-yl (–CH(OCH$_3$)–C$_6$H$_4$–F) | IR $\nu_{max}^{film}$ (cm$^{-1}$): 1765, 1700 |
| 24 | norbornane-fused dicarboximide | —(CH$_2$)$_4$— | 4-(4-fluorophenylsulfinyl)piperidin-1-yl (–SO–C$_6$H$_4$–F) | M.P. 197–198° C. (HCl) |

TABLE 7-continued $$\underset{A}{\overset{B}{\diagdown}}N-W-N\underset{\diagup}{\overset{\diagdown}{\bigcirc}}G \qquad (I)$$

| Compound No. | $\underset{A}{\overset{B}{\diagdown}}\overset{O}{\underset{\diagup}{\parallel}}N-$ | —W— | —N⟨piperidine⟩G | Physical property |
|---|---|---|---|---|
| 25 | norbornane-dicarboximide | —(CH$_2$)$_4$— | 4-(4-fluorophenoxy)piperidinyl | M.P. 207–209° C. (HCl) |
| 26 | cis-hexahydrophthalimide | —(CH$_2$)$_4$— | 4-(4-fluorophenoxy)piperidinyl | M.P. 199–200° C. (HCl) |
| 27 | cis-hexahydrophthalimide | —(CH$_2$)$_4$— | 4-(4-fluorophenylsulfinyl)piperidinyl | M.P. 181–182° C. (HCl) |
| 28 | 3,3-tetramethyleneglutarimide | —(CH$_2$)$_4$— | 4-(4-fluorobenzoyl)piperidinyl | M.P. 226–229° C. (HCl) |
| 29 | saccharin | —(CH$_2$)$_4$— | 4-(4-fluorobenzoyl)piperidinyl | M.P. 226–229° C. (HCl) |
| 30 | cis-hexahydrophthalimide | —(CH$_2$)$_2$— | 4-(4-fluorobenzoyl)piperidinyl | M.P. 236–240° C. (HCl) |
| 31 | cis-hexahydrophthalimide | —(CH$_2$)$_5$— | 4-(4-fluorobenzoyl)piperidinyl | M.P. 196–198° C. (HCl) |

TABLE 7-continued
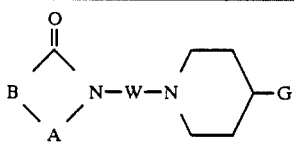
(I)
| Compound No. | 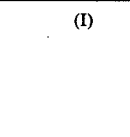 | —W— | 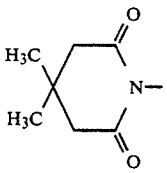 | Physical property |
|---|---|---|---|---|
| 32 | 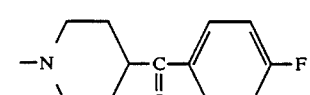 | —(CH$_2$)$_4$— | 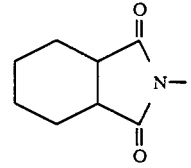 | M.P. 238–240° C. (HCl) |
| 33 | 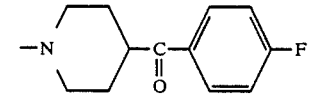 | —(CH$_2$)$_3$— | 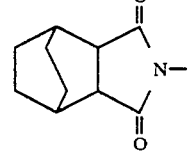 | M.P. 239–241° C. (HCl) |
| 34 | 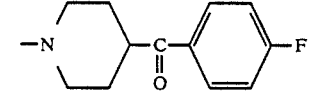 | —(CH$_2$)$_4$— | 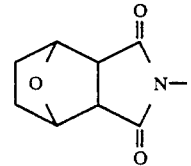 | M.P. 254–255° C. (HCl) |
| 35 | 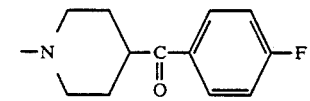 | —(CH$_2$)$_4$— | 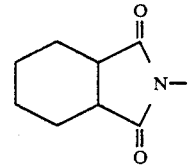 | M.P. 230–231.5° C. (HCl) |
| 36 | 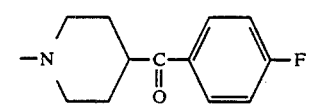 | —CH$_2$— | 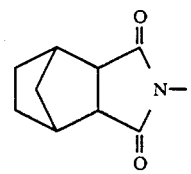 | M.P. 160–163° C. (HCl) |
| 37 | 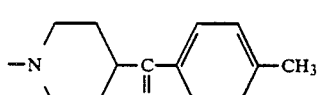 | —(CH$_2$)$_4$— | 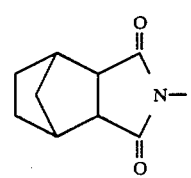 | M.P. 117–118° C. |
| 38 | 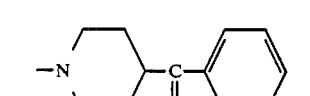 | —(CH$_2$)$_4$— | | M.P. 102–103° C. |

TABLE 7-continued $$\underset{A}{\overset{B}{\bigg|}}\text{N}-\text{W}-\text{N}\underset{}{\bigcirc}\text{G} \quad (I)$$
(with C=O bridge on B-N)

| Compound No. | B–A–N (with C=O) | —W— | N-piperidine-G | Physical property |
|---|---|---|---|---|
| 39 | norbornane-dicarboximide | —(CH$_2$)$_4$— | 4-(4-bromobenzoyl)piperidine | M.P. 147–147.5° C. |
| 40 | norbornane-dicarboximide | —(CH$_2$)$_4$— | 4-(4-methoxybenzoyl)piperidine | M.P. 120–121° C. |
| 41 | norbornane-dicarboximide | —(CH$_2$)$_4$— | 4-[(4-fluorophenyl)(hydroxyimino)methyl]piperidine | M.P. 207–207.5° C. (HCl; stereo isomer of hydroxyimino group) |
| 42 | norbornane-dicarboximide | —(CH$_2$)$_4$— | 4-[(4-fluorophenyl)(hydroxyimino)methyl]piperidine | M.P. 220.5–221° C. (HCl; stereo isomer of hydroxyimino group) |
| 43 | norbornane-dicarboximide | —CH$_2$CH(OH)CH$_2$CH$_2$— | 4-(4-fluorobenzoyl)piperidine | M.P. 138–140° C. |
| 44 | norbornene-dicarboximide | —CH$_2$CH$_2$CH(OH)CH$_2$— | 4-(4-fluorobenzoyl)piperidine | M.P. 112–114° C. |
| 45 | norbornane-dicarboximide | —CH$_2$CH$_2$CH(OH)CH$_2$— | 4-(4-fluorobenzoyl)piperidine | M.P. 171–172° C. |

TABLE 7-continued

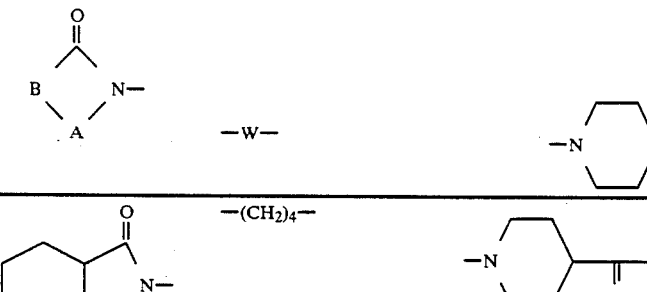

| Compound No. | B−A (with N, C=O) | —W— | —N-piperidine-G | Physical property |
|---|---|---|---|---|
| 46 | 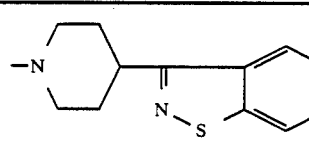 | —(CH$_2$)$_4$— | 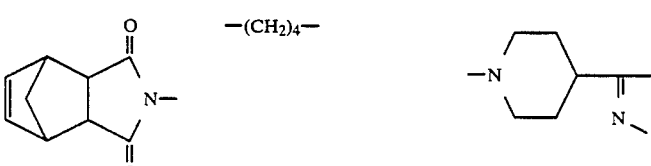 | M.P. 216–217° C. (HCl) |
| 47 | 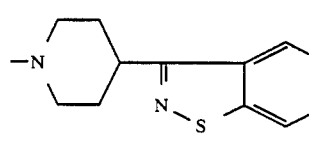 | —(CH$_2$)$_4$— | 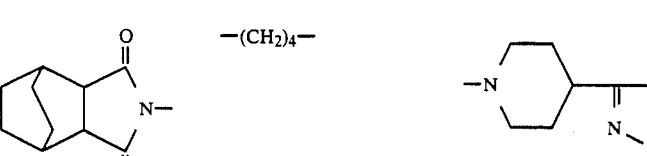 | M.P. 226–228° C. (HCl) |
| 48 | 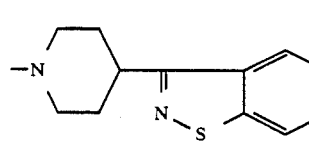 | —(CH$_2$)$_4$— | 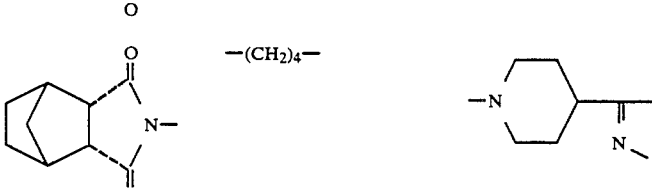 | M.P. 213–215° C. (HCl) |
| 49 | 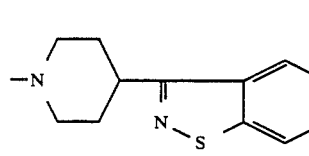 | —(CH$_2$)$_4$— | 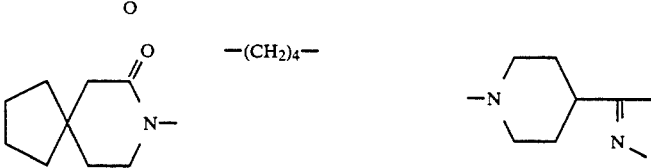 | M.P. 224–226° C. (HCl) |
| 50 | 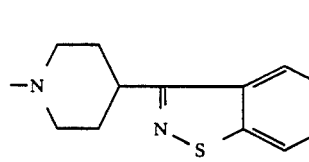 | —(CH$_2$)$_4$— | 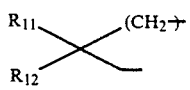 | M.P. 197–199° C. (HCl) |

What is claimed is:

1. A compound of the formula:

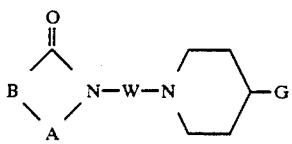

wherein
A is a carbonyl group;
B is a group of the formula:

$$\begin{array}{c} R_{11} \\ R_{12} \end{array} \diagdown \diagup (CH_2)_n$$

(in which R$_{11}$ and R$_{12}$ are each lower alkyl group, or they are combined together to form a lower alkylene group;
W is trimethylene, propylene, tetramethylene, 2-methyltrimethylene or 2-methyltetramethylene, or a lower alkenylene group, a lower alkynylene group or a lower alkylene group substituted with hydroxyl; and
G is a benzoisothiazolyl group, a benzoisothiazolyl group substituted with a member selected from the group consisting of lower alkyl, lower alkoxy, halogen and halogenated lower alkyl or a group of the formula:

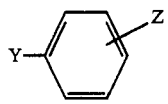

(in which Y is an oxygen atom, a carbonyl group, a methylene group, a group of the formula:

(in which m is an integer of 0, 1 or 2), a group of the formula:

(in which $R_{13}$ is a hydrogen atom, a lower alkyl group or a lower alkanoyl group) or a group of the formula:

and Z is a hydrogen atom, a halogen atom, a lower alkyl group or a lower alkoxy group), or its pharmaceutically acceptable salt.

2. The compound according to claim 1, wherein $R_{11}$ and $R_{12}$ are each a lower alkyl group.

3. The compound according to claim 1, wherein W is tetramethylene or either one of the following groups: $-CH_2CH=CHCH_2-$, $-CH_2C\equiv CCH_2$, $-CH_2CH(OH)CH_2CH_2-$ and $-CH_2CH_2CH(OH)CH_2-$.

4. The compound according to claim 1, wherein G is a group of the formula:

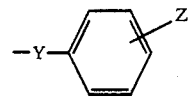

(in which Y is a carbonyl group and Z is a halogen atom, a lower alkyl group or a lower alkoxy group), or a benzoisothiazolyl group or a benzoisothiazolyl group substituted with a member selected from the group consisting of lower alkyl, lower alkoxy, halogen and halogenated lower alkyl.

5. The compound according to claim 1, wherein B is a group of the formula:

(in which $R_{11}$ and $R_{12}$ are each a lower alkyl group), W is a lower alkyl group, W is tetramethylene and G is a group of the formula:

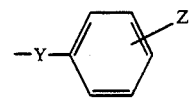

(in which Y is a carbonyl group and Z is a halogen atom).

6. The compound according to claim 1, wherein said pharmaceutically acceptable salt is a salt with an acid selected from the group consisting of hydrochloric acid, hydrobromic acid, hydroiodic acid, sulfuric acid, acetic acid, oxalic acid, citric acid malic acid, maleic acid, tartaric acid, and fumaric acid.

7. A pharmaceutical composition for the treatment of psychosis which comprises as an active ingredient a pharmaceutically effective amount of at least one compound as claimed in claim 1, and at least one pharmaceutically acceptable inert carrier or diluent.

8. A method for the treatment of psychosis which comprises administering to a person suffering from psychosis a pharmaceutically effective amount of at least one compound as claimed in claim 1.

* * * * *